US011452861B2

United States Patent
Garrigue et al.

(10) Patent No.: US 11,452,861 B2
(45) Date of Patent: Sep. 27, 2022

(54) SUTURELESS ANCHORING DEVICE FOR HEART PUMP

(71) Applicant: FINEHEART, Pessac (FR)

(72) Inventors: Stéphane Garrigue, Begles (FR); Arnaud Mascarell, Montbazon (FR)

(73) Assignee: FINEHEART, Pessac (FR)

( * ) Notice: Subject to any disclaimer, the term of this patent is extended or adjusted under 35 U.S.C. 154(b) by 779 days.

(21) Appl. No.: 16/467,939

(22) PCT Filed: Nov. 20, 2017

(86) PCT No.: PCT/FR2017/053181
§ 371 (c)(1),
(2) Date: Sep. 30, 2019

(87) PCT Pub. No.: WO2018/104605
PCT Pub. Date: Jun. 14, 2018

(65) Prior Publication Data
US 2020/0023108 A1  Jan. 23, 2020

(30) Foreign Application Priority Data
Dec. 9, 2016  (FR) ..................... 16 62268

(51) Int. Cl.
*A61M 60/857* (2021.01)
*A61M 60/861* (2021.01)
(Continued)

(52) U.S. Cl.
CPC ....... *A61M 60/857* (2021.01); *A61B 17/3423* (2013.01); *A61M 60/148* (2021.01);
(Continued)

(58) Field of Classification Search
CPC .............. A61M 60/148; A61M 60/165; A61M 60/861; A61B 2017/3425
See application file for complete search history.

(56) References Cited

U.S. PATENT DOCUMENTS 5,338,308 A * 8/1994 Wilk ..................... A61M 25/02
604/523
5,823,956 A * 10/1998 Roth .................. A61B 18/1482
606/41

(Continued)

OTHER PUBLICATIONS

International Search Report, dated Jan. 12, 2018, from corresponding international application No. PCT/FR2017/053181.

*Primary Examiner* — Nicholas W Woodall
(74) *Attorney, Agent, or Firm* — Nixon & Vanderhye (57) ABSTRACT

A sutureless securing device for securing on an opening in a ventricular wall, includes: a hollow main body with an outer surface; a ring received at a first end of the hollow body, this ring being mobile along part of the outer surface of the hollow body; a tubular membrane covering the outer surface, whilst extending between the ring and the second end of the hollow body; a distal end of this tubular membrane, placed on the side of this second end, being self-expandable between a first configuration in which it has a tubular form, and a second configuration in which it defines a first flange extending radially, starting from the hollow body; the other end of this tubular membrane being able to be deformed by the displacement of the ring, such as to form a retention flange, the position of which can vary relative to the first flange.

20 Claims, 3 Drawing Sheets

(51) Int. Cl.
*A61M 60/148* (2021.01)
*A61B 17/34* (2006.01)
*A61M 60/165* (2021.01)

(52) U.S. Cl.
CPC ........ *A61M 60/165* (2021.01); *A61M 60/861* (2021.01); *A61B 2017/3425* (2013.01); *A61B 2017/3488* (2013.01)

(56) References Cited

U.S. PATENT DOCUMENTS

| | | | |
|---|---|---|---|
| 2004/0092985 A1* | 5/2004 | Parihar | A61B 17/3415 606/167 |
| 2007/0078302 A1* | 4/2007 | Ortiz | A61B 17/3421 600/115 |
| 2007/0106315 A1* | 5/2007 | Gregoric | A61M 60/148 606/158 |
| 2010/0249491 A1* | 9/2010 | Farnan | A61M 60/148 600/16 |
| 2014/0378772 A1 | 12/2014 | Sundt, III et al. | |
| 2015/0196321 A1* | 7/2015 | Gregory | A61M 60/857 606/108 |
| 2021/0393943 A1* | 12/2021 | Najmabadi | A61M 60/17 |

* cited by examiner

SUTURELESS ANCHORING DEVICE FOR HEART PUMP

BACKGROUND OF THE INVENTION

Field of the Invention

The present invention relates to a sutureless securing device for securing on an opening in a ventricular wall, in particular for the purpose of fitting a heart pump in this opening.

It also relates to an assembly for fitting/removing such a heart pump in this securing device.

Technological Background

Cardiac insufficiency (CI) is a pathological state in which the heart of the patient is unable to supply a flow of blood necessary for the metabolic needs of the organism.

In order to treat cardiac insufficiency, it is known to implant a ventricular assistance device (VAD), which is an artificial heart pump.

This mechanical pump does not replace the heart, which continues to function, but provides assistance for the weakened ventricle so as to increase the flow of blood in a manner which is adapted to the needs of the individual.

This assistance can be temporary, whilst waiting for a transplant available to carry out a heart transplant.

However, it is found that a significant proportion of patients will not receive such a transplant, either because they are unable to undergo a transplant of this type, for example because of severe cardiac insufficiency, or because no suitable transplant is available for these patients.

In this case, the ventricular assistance is used as the intended purpose, i.e. the artificial heart pump is implanted on a long-term basis.

These heart pumps thus form the subject of intensive research aimed at improving the survival and quality of life of patients with cardiac insufficiency.

Many advances have been made in recent years, and ventricular assistance devices are now known which are more compact, silent, and with an increased service life.

The implantable heart pumps according to the prior art are thus typically equipped with an integrated electric motor in order to ensure their operation, with the speed of rotation of the pump supplying the force necessary to make the blood circulate from the weakened ventricle to the circulation of the body.

Systems are known for implantation of pumps of this type in an orifice in a ventricular wall.

These implantation systems generally comprise a tubular portion, at the ends of which there are placed or formed collars which are each designed to be placed against an opposite face of the ventricular wall, after introduction of the tubular portion into an orifice provided in this ventricular wall.

These collars thus make it possible to retain in position this hollow tubular portion, which then defines an open duct passing through the ventricular wall.

At the end of this tubular portion, which is placed on the exterior of the heart, an aspiration pump is fitted, which ensures the return of the blood which is present in the ventricle, to the circulation of the body.

Although representing a certain amount of progress for the quality of life of patients suffering from cardiac insufficiency, numerous disadvantages are still encountered.

In particular, with these implantation systems according to the prior art, damage caused to the ventricular wall during the installation of the systems is observed, which damage can give rise to local tearing of this wall.

Purely by way of illustration, an implantation system of this type is known, one of the flanges of which is placed against a face of the ventricular wall by means of displacement of the flange along the outer surface of the tubular portion. It is then found that, since the operator cannot control precisely the forces applied on the ventricular wall during the abutment of this flange against the face of the wall, the flange typically compresses the wall and damages it.

In addition, since the dimensions of the flanges are reduced in order to allow them to pass through the orifice, the mechanical strength of the implantation system is limited, and for example does not permit the application of substantial forces on the system once it is in place on the ventricular wall.

Also, since the pump is placed at the end of the tubular portion, on the exterior of the heart, and the blood which is present in the ventricle passes into the open duct, there is a risk of loss of blood, in particular because of the forces applied to the ventricular wall.

There is therefore a pressing need for a device for securing on an orifice of a ventricular wall, the original design of which overcomes the above-described disadvantages.

Subject of the Invention

The objective of the present invention is to eliminate the disadvantages of the prior art, and to comply with the aforementioned constraints, by proposing a sutureless securing device for securing on an opening of a ventricular wall, having a simple design and operative mode, which device is reliable, and preserves the ventricular wall, i.e. is not able to damage this wall.

Another objective of the present invention is a securing device of this type which is adjustable to different thicknesses of ventricular wall.

Yet another objective of this invention is a device of this type making it possible to accommodate a heart pump therein and to permit maintenance operations on this pump.

The objective of the present invention is also a fitting/removing device making it possible, easily and without risk of reflux of blood, to fit and remove a heart pump in and from this securing device.

BRIEF DESCRIPTION OF THE INVENTION

For this purpose, the invention relates to a device for securing on an opening in a ventricular wall, comprising:
  a hollow main body with a generally cylindrical form with an outer surface;
  a ring which is received at a first end of said hollow body, this ring being mobile along at least part of the outer surface of the hollow body;
  a tubular membrane covering the outer surface of the outer body, whilst extending between said ring and the end opposite the first end of the hollow body, known as the second end;
  a distal end of this tubular membrane, placed on the side of said second end of the hollow body, being self-expandable between a first configuration in which it has a tubular or substantially tubular form, and a second configuration in which it defines a first flange extending radially, or substantially radially, starting from said hollow body, this first flange being designed to abut a face of said ventricular wall;

the other end, known as the proximal end, of this tubular membrane being able to be deformed by the displacement of said ring along the outer surface of the hollow body, such as to form a retention flange, the position of which can vary relative to said first flange, so as to adapt to ventricular walls with different thicknesses;

said retention flange being designed to come into contact with the opposite face of said ventricular wall, such that said flanges and the assembly formed by the part of the hollow body and the portion of the tubular membrane covering it, passing through said ventricular wall through said opening, lock said securing device in position in said opening.

This ring, known as a pressing ring, has a form suitable for engaging on the outer surface of said hollow body. It is placed at, or in the vicinity of, said first end of the hollow body.

Advantageously, this ring makes it possible to compress the tubular membrane placed on the outer surface of said hollow body. The degree of compression, or pressing, of the tubular membrane, is controlled by the operator by displacing the ring to a greater or lesser extent along the outer surface of the hollow body. The forces applied on the ventricular wall are thus advantageously controlled.

For this purpose, on its edge which is designed to come into contact with the proximal end of said tubular membrane, the ring has an annular surface for pressing said tubular membrane. This annular surface can comprise a receptacle for receipt of the proximal end of the tubular membrane.

The proximal end of the tubular membrane can thus be deformed by widening towards the exterior such as to form a retention flange spaced from the first flange.

This radially widened flange advantageously has a planar or substantially planar surface which is designed to face the ventricular wall.

The hollow body has a longitudinal dimension larger than that of the opening extending between the opposite faces of the ventricular wall, and a diameter which is the same as, or larger than, that of the opening in the ventricular wall.

Thus, and advantageously, the device for securing on an opening in a ventricular wall ensures sealing after being fitted, without any suture being performed, contrary to the anchorage devices of the prior art. In this respect, the device in question is for securing on ventricular puncture with a diameter larger than 20 mm, which does not require any stitch.

In different particular embodiments of this device, each having its particular advantages and being able to be subjected to numerous possible technical combinations:

the proximal end of the tubular membrane is configured to be deformed progressively during the displacement of the ring, such as to form a retention flange, the position of which can vary within a predetermined range of distances starting from the first flange;

said ring comprises on its periphery at least one coupling finger which is designed to cooperate with notches placed in the outer surface of said hollow body. This therefore results in discrete or intermittent displacement of the ring along the outer surface of the hollow body.

Alternatively, with the outer surface of said hollow body comprising a thread on at least part of its outer surface, the inner surface of said ring comprises a thread which is configured to cooperate with said thread placed on the outer surface of the hollow body, in order to permit the displacement of said ring;

said ring comprises a non-return finger in order to prevent any loosening of the ring after formation of the retention flange;

the outer surface of the hollow body comprises a stop in order to prevent the displacement of said ring;

said ring and said hollow body are made of rigid materials which are inert for the human body;

said tubular membrane is made of nitinol, of a nitinol alloy, or also of expandable polyurethane;

the device is configured to form a retention flange with an outer diameter which is strictly larger than 3/2 D, where D is the diameter of the opening in the ventricular wall.

Preferably, the retention flange thus formed has an outer diameter of between 3/2 D and 3 D.

Purely by way of illustration, this retention flange has a diameter of 40 mm. This large dimension of the retention flange designed to be formed thus reinforces the support of the device on the ventricular wall, and consequently ensures better retention in position, or stabilization, of the securing device on this ventricular wall, in particular during intervention on the propulsive heart pump which is designed to be received in the channel of this main body.

Furthermore, any stresses are distributed over a larger surface area of the ventricular wall, such that the risk of damaging this wall is reduced, or even eliminated;

with the inner wall of the hollow body delimiting a channel extending between the first and second ends of the hollow body, said inner wall comprises means for sealed assembly of the body of a heart pump and said wall, said heart pump thus being received at least partly in said channel. The diameter of the channel is equal, or substantially equal, to the outer diameter of the body of the pump, in order to accommodate the pump in said channel.

Preferably, with the body of the pump which is designed to be accommodated in the channel delimited by the inner wall of the hollow body comprising a thread on its outer surface, this inner wall comprises a thread which is designed to cooperate with the thread of the pump body;

said heart pump is an implantable ventricular assistance device (VAD).

Preferably, it is a propulsive heart pump.

With this heart pump being anchored to the wall of the heart by means of the securing device, the patient can thus move actively without any risk.

The first end of the hollow main body comprises an opening which is in communication with the channel delimited by the inner wall of the hollow body.

Advantageously, one or a plurality of wired connections such as wires can pass through this opening in order to connect an artificial heart pump accommodated in this channel to a control unit of this pump. Signals for control of this pump can thus be sent to the artificial pump.

This control unit can also comprise a wireless emitter-receiver to transmit automatically data such as information on the rate of heartbeat or the state of the supply source implanted, for the purpose of remote medical monitoring.

Data can be transmitted to a portable external terminal by means of short-range wireless communication signals, for example based on a Bluetooth or Zigbee protocol, etc. This external terminal can comprise a means for communication which implements a cellular access network and/or an Internet network, in order to transmit this data to a cardiologist for example. The cellular access network can be of several types (2G, 3G, 4G), with each type of network being accessible according to a plurality of cellular access technologies (2G: EDGE, GPRS, 3G: UMTS, HSDPA, HSUPA, HSPA, HSPA+, 4G: LTE). The Internet network is for example a network comprising wireless non-cellular access points such as a WLAN network, for example Wi-Fi or WiMAX or also a Li-Fi network. This external terminal can have a display device in order to allow the user to read messages or choose options from a menu.

Preferably, this central unit comprises one or a plurality of inputs for receipt of one or a plurality of signals, each of which is associated with an audible or inaudible mechanical vibration associated with the mechanical activity of the heart, said central unit comprising a first sub-set of software instructions of said set of software instructions which, when they are executed by said processor, are configured to define a temporal window for measurement of said signal(s) in order to analyze each signal thus received at the input of said central unit during this temporal window, so as to determine one or a plurality of parameters of the corresponding signal, in order to compare the parameter(s) of each signal thus determined with one of a plurality of items of data previously recorded in a storage unit of said central unit, so as to identify the signal corresponding to the closure of the mitral valve, as well as the instant $t_1$ corresponding to the closure of said mitral valve.

The present invention also relates to a ventricular assistance unit comprising a propulsive heart pump and a device for securing on an opening in a ventricular wall, as previously described.

Advantageously, this propulsive heart pump is accommodated inside the channel delimited by the inner wall of the hollow main body. Preferably, the pump body and the inner wall of the hollow main body are assembled in a sealed manner so as to prevent any reflux of blood.

The present invention also relates to an assembly for fitting/removing a heart pump on a securing device as described above, said assembly comprising a guide element with a distal end, a proximal end, and a lumen extending between, and opening at, said distal and proximal ends, said heart pump having a pump body.

According to the invention,
with said pump body comprising a recess
said assembly comprises a gripping unit which can slide in said lumen, said gripping unit comprising at its free end a part which is complementary with said recess in such a way as to ensure the engagement of this free end and of the pump body for the gripping and displacement of said heart pump.

Preferably, with said recess being a hollow, or a projection, formed on or in the pump body, said complementary part is a head with a form paired with said hollow, or respectively a hollow with a form paired with said projection, for assembly of said free end on said pump body.

Advantageously, the free end of said gripping unit comprises a polygonal profile which is complementary with a hollow profile placed at an end of the heart pump body, such that this free end can be inserted in said hollow profile.

Advantageously, with said pump body comprising a thread on a part of its outer surface, which is distinct from said recess, said gripping unit is an elongate body of general cylindrical shape, so as to be maneuverable in rotation in said lumen in order to screw/unscrew said pump body on a complementary thread carried by the inner wall of the hollow body. The gripping unit can thus be a hollow tube or a rod whose free ends are parts complementing the recess of a pump body in order to authorize its manipulation.

Preferably, with said pump body comprising at least two recesses, said free end of said gripping unit comprises, for each recess, an assembly part complementing the corresponding recess.

This assembly can comprise a sealing element placed inside said lumen, preferably in the distal part thereof, this sealing element being open when the free end of said gripping unit is pressed against it, in order to free the passage of said gripping unit through this sealing element.

Preferably, this sealing element comprises a flap valve whose seat is inclined at 45° in order to facilitate the passage of the medical device, while preventing the passage of blood in the other direction when this flap valve is in its closure position. This flap valve thus defines a non-return valve.

Preferably, the distal end of said guide element comprises a device for stabilization of part of the heart, said stabilization device comprising a widened part, which preferably comprises at its end with the widest diameter a groove which has at least one aspiration orifice for creation of a vacuum in said groove when a portion of the ventricular wall is in contact with said stabilization device.

BRIEF DESCRIPTION OF THE DRAWINGS

Other advantages, objectives and particular characteristics of the present invention will become apparent from the following description, provided by way of explanation which is in no way limiting, with reference to the appended drawings in which.

DETAILED DESCRIPTION OF AN EMBODIMENT OF THE INVENTION

Firstly, it should be noted that the figures are not to scale.

FIGS. 1 to 5 show schematically a device 10 for anchorage without suture of a propulsive heart pump in an opening in a ventricular wall, according to a particular embodiment of the present invention.

This anchorage device 10 comprises a tube with an outer surface 11 and an inner surface 12 delimiting a channel extending between a first end 13 and a second end 14 of this tube, which ends are open.

The outer 11 and inner 12 surfaces of this tube 10 have a thread, the outer surface 11 of the tube comprising on the side of its second end 14 a portion of wall with an excess thickness which is not threaded, and is connected by a shoulder to the remainder of the outer surface 11 of the threaded tube. This shoulder thus defines a stop in order to limit the displacement of a pressing ring 15 received at the first end 13 of the tube.

The inner surface of this ring 15 comprises a thread (not represented) which is designed to cooperate with the thread of the outer surface 11 of the tube, in order to permit continuous displacement of this ring 15 along part of the outer surface 11 of this tube.

Between this ring 15 and the second end 14 of the tube, a tubular membrane 16 is placed, which covers the outer surface 11 of the tube.

The ring 15 comprises on its face which is designed to press the tubular membrane 16 a receptacle such as a groove, in order to receive the corresponding free end of the tubular membrane 16. Advantageously, this end of the tubular membrane 16, which is also known as the proximal end, is not rendered integral in its receptacle in order to prevent torsions of the membrane.

A distal end 17 of this tubular membrane 16, placed on the side of the second end 14 of the tube, is self-expandable between a first stable configuration in which it has a tubular form, and a second stable configuration in which it defines a first flange 18 extending radially from said tube.

Figure 1:
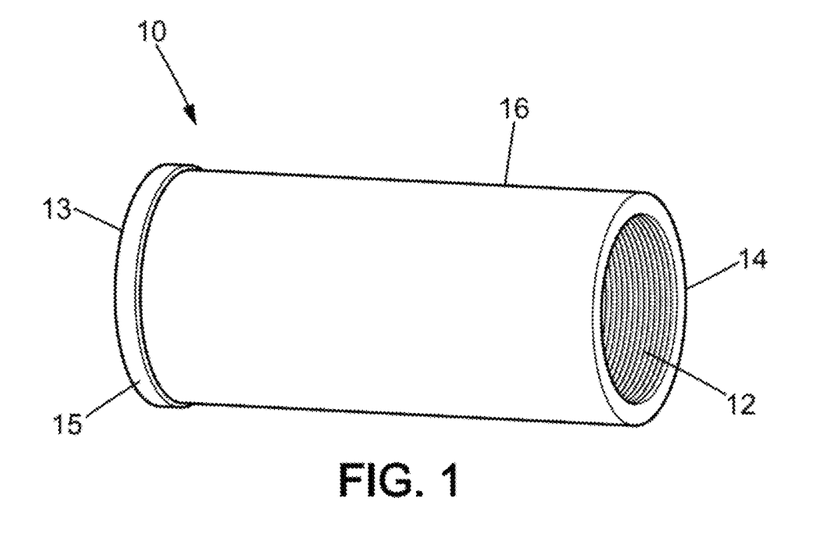
FIG. 1 represents schematically a device for anchorage without suture for a propulsive heart pump according to a particular embodiment of the invention; the distal end of the tubular membrane being in its first stable configuration, and the ring not yet having been displaced along the outer surface of the tube, in order to compress the proximal end of the tubular membrane.
Figure 3:
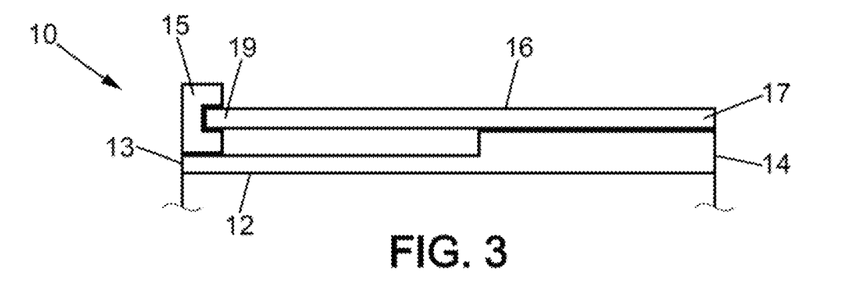
FIG. 3 is a partial schematic representation in cross-section of the anchorage device illustrated in FIG. 1.

The first stable configuration of the membrane advantageously permits easy introduction of the second end 14 of the tube through the opening in the ventricular wall.

Figure 2:
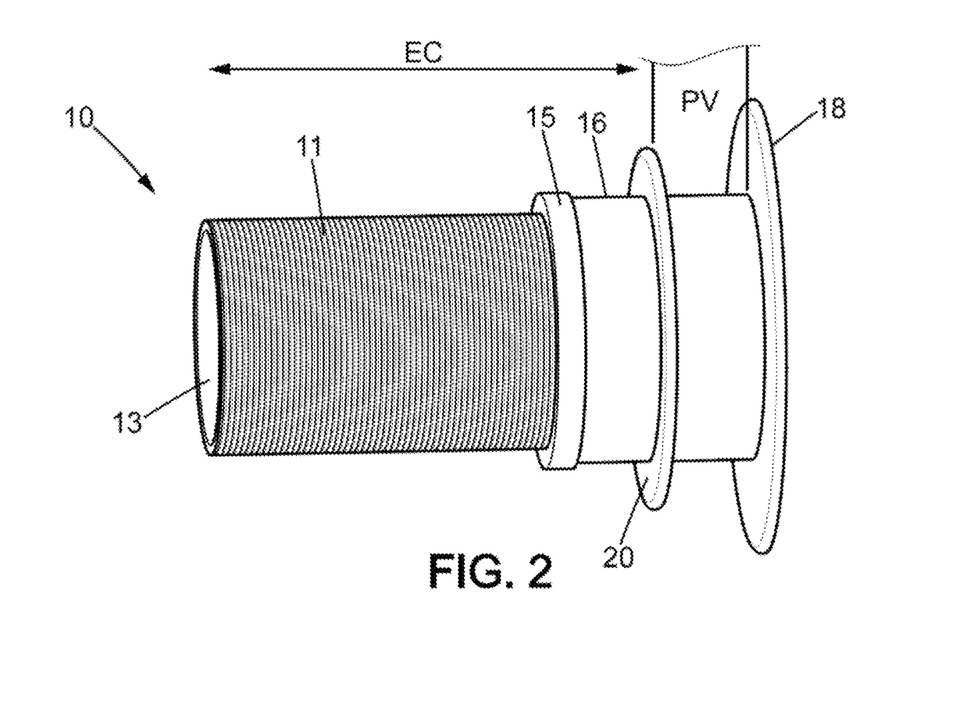
FIG. 2 shows the device for anchorage without suture in FIG. 1 in an activated state, in which the distal end of the tubular membrane is in its second stable configuration, and the proximal end of the tubular membrane has been deformed in order to define a retention flange; the opposite faces of a ventricular wall (PV) have been schematized in the upper part of the device in order to illustrate the putting into contact of the flanges on these opposite faces, with the extra-cardiac space (EC) also being shown.
Figure 4:
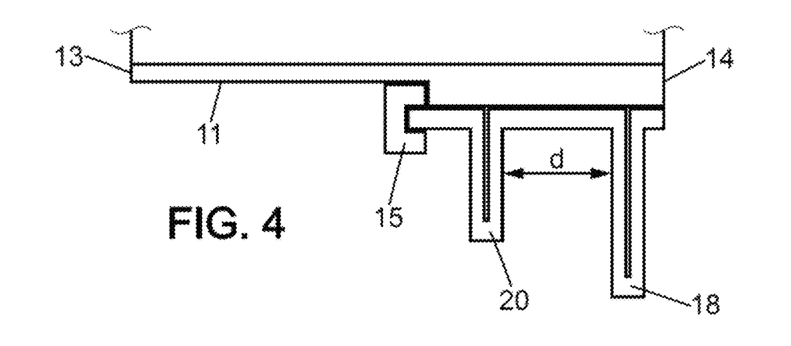
FIG. 4 is a partial schematic representation in cross-section of the anchorage device illustrated in FIG. 2.

The second stable configuration of the tubular membrane 16 makes it possible to generate a first flange 18, such that the flange abuts, or is placed against, a face of the ventricular wall, when the tube has been introduced through the opening in this ventricular wall.

The transition from the first stable configuration to the second stable configuration is obtained by means of an increase in the temperature of the tubular membrane 16, for example by exposing it to the temperature of the human body, the tubular membrane 16 being made of nitinol or expanded polyurethane, which is a form memory material.

The opposite end, known as the proximal end 19, of this tubular membrane 16, is able to be deformed progressively by the displacement of the ring 15 along the outer surface 11 of the tube, such as to form a second retention flange 20, the position of which can vary within a predetermined range of distances d starting from the first flange 18 defined by the distal end 17 of the tubular membrane 16 in its second stable configuration. This distance d makes it possible to compress the ventricular wall in order to ensure the sealing of the device, as well as reliable and durable retention.

It is thus possible to adapt the anchorage device 10 to ventricular walls with different thicknesses. The shoulder determined by the profile of the outer surface 11 of the tube advantageously makes it possible to define an upper limit for the compression of the tubular membrane 16, and thus to limit the forces applied on the ventricular wall.

Figure 5:
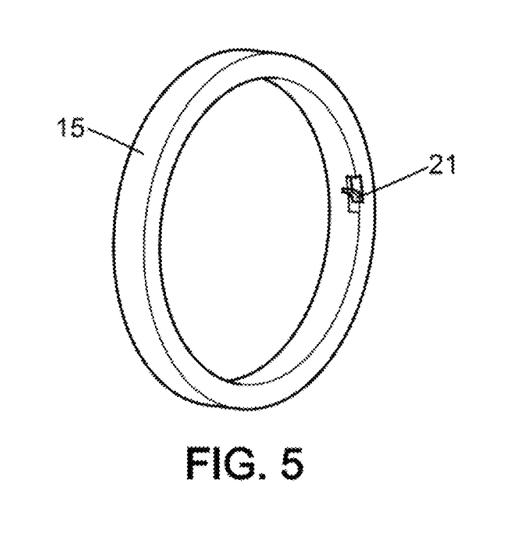
FIG. 5 is a view in perspective of the ring of the anchorage device in FIG. 1, showing the non-return valve of the ring.

Advantageously, this ring 15 comprises a non-return finger 21.

This non-return finger 21 makes it possible to prevent any loosening of the ring 15 after formation of the second retention flange 20, which would be liable to give rise to release, or partial release, from the stresses in the tubular membrane 16, with the consequence of subsidence of the second retention flange 20. Deformation of this type of the second retention flange 20 would be liable to give rise to poorer sealing of the connection between the anchorage device and the ventricular wall, which would be liable to result in leakages of blood.

The ring 15 and the tube are made of rigid, inert materials, i.e. which are biocompatible with the human organism. They are for example made of PEEK (polyetheretherketone), of ceramic or of titanium. These elements can be printed, i.e. they are then formed by a three-dimensional printing process.

Once this anchorage device 10 has been rendered integral with the ventricular wall, it is possible to introduce a propulsive heart pump into the channel delimited by the inner surface 12 of the tube.

This pump (not represented) is advantageously designed to be received in the channel of the tube, such that it does not form a projection outside the tube outside the heart.

In addition, the assembly of the pump body and the inner surface 12 of the tube is sealed in order to prevent any reflux of blood via this channel. An assembly of this type is advantageously formed in this case by screwing the pump body onto the thread supported by the inner surface 12 of the tube.

For this purpose, the pump body has on at least part of its outer surface 11 a thread which is designed to cooperate with the thread supported by the inner surface 12 of the tube.

The screwing of the pump into the inner surface 12 of the tube also makes it possible to regulate or adjust the positioning of this pump relative to the aortic valve, and consequently to optimize the position of this heart pump so as to obtain a better hemodynamic performance. Advantageously, this therefore provides an optimized cardiac output, which is made possible by the possibility of creating continuous, and consequently extremely precise, displacement of the pump body along the thread formed on the inner surface 12 of the tube.

Thus, and more generally, the present invention also relates to a method designed to optimize the hemodynamic performance, wherein there is adjustment of the position of a heart pump implanted on a ventricular wall relative to the aortic valve of the patient. Preferably, this adjustment is obtained by a displacement of the heart pump relative to this aortic valve. More preferably, this adjustment is carried out by screwing/unscrewing the body of the pump along a threaded inner surface, or on the threaded inner side, of a tubular wall of a securing or anchorage device secured in an opening in a ventricular wall, the pump body comprising for this purpose on its outer surface a thread which is complementary with the thread of the threaded inner side of the tubular wall, and is designed to cooperate with the latter. An adjustment of the position of this type is advantageously very precise because of the continuous displacement of the heart pump permitted by these threads.

The objective is thus to position the end of the heart pump in order to direct the blood propelled by this pump to the aortic valve of the patient. Preferably, the objective is to place this end of the heart pump at a distance of between 10 mm and 20 mm from the aortic valve.

In order to limit the displacement of the heart pump by screwing the pump along the inner surface 12 of the tube, this inner surface 12 of the tube can comprise at least one stop. It is thus possible to control the intraventricular advance of the heart pump.

Figure 6:
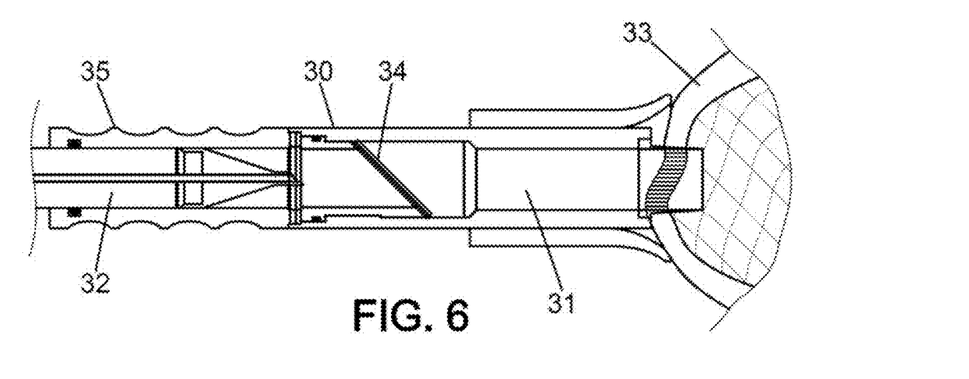
FIG. 6 is a view in longitudinal cross-section of a fitting/removing assembly of a heart pump connected to the apex of a beating heart, according to a particular embodiment of the invention, this assembly being shown in a first configuration in which it comprises a tool for perforation and ablation of part of the ventricular wall, in order to create an opening in said wall.
Figure 7:
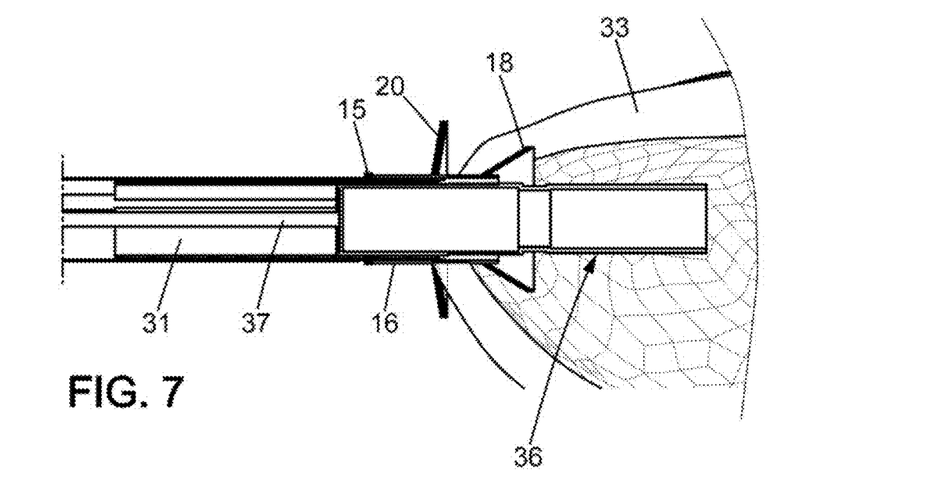
FIG. 7 is a view in longitudinal cross-section of the fitting/removing assembly in FIG. 6 according to another configuration in which it comprises a gripping unit connected to and supporting a heart pump, which is engaged in an anchorage device secured in the opening in a ventricular wall, part of the heart pump being intraventricular.
Figure 8:
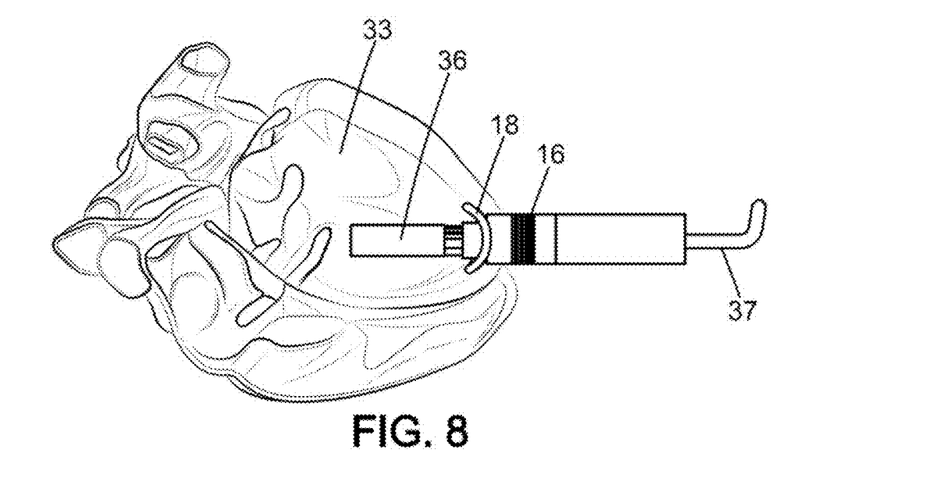
FIG. 8 represents, partially and schematically, the fitting/removing assembly for a heart pump of FIG. 7, the heart pump being mounted inside the ventricle.

FIGS. 6 to 8 illustrate a system for introduction of a medical device such as a needle, a device 10 for anchorage on an orifice in a ventricular wall as described above, a heart pump 36, or also a unit for gripping this pump, according to a particular embodiment of the present invention.

This system for the introduction of a medical device comprises a main body 30 defining a longitudinal inner channel or lumen 31 for receipt of this medical device 32, this medical device being mobile in translation in this inner channel 31, such that a part of it can be placed projecting from this main body 30, for its introduction into a ventricular wall 33 or into the channel delimited by the inner wall 12 of a sleeve secured in the opening in the ventricular wall 33, such as that of an anchorage device described above.

This main body 30 also comprises a sealing element 34, which is placed inside this channel, such that this sealing element 34 can be open when the end of the medical device is pressed against it, in order to open up the passage for the medical device 32 through this sealing element 34.

In this case, this sealing element 34 comprises a flap valve, the seat of which is inclined by 45° in order to facilitate the passage of the medical device 32, whilst preventing the passage of the blood in the other direction when this flap valve is in its closure position. This flap valve thus forms a non-return valve.

The proximal end of the main body 30 comprises a gripping handle 35, and the distal end of the main body advantageously comprises a venting valve (not represented) in order to eliminate the presence of any air in the part of the inner channel positioned downstream from the sealing element 34.

In order to manipulate the heart pump 36 for its implantation in, or its disassembly from, the channel delimited by the inner wall 12 of the tube, this system comprises a gripping unit 37 which can slide in the inner channel 31, this gripping unit 37 having at its free end a part which is complementary with a recess contained in the pump body.

It is thus possible to ensure the engagement of the free end of this gripping unit 37 and the recess in the pump body, for gripping and manipulation of the heart pump 36.

Purely by way of illustration, with the pump body having a hollow polygonal recess such as one with six facets provided in a hollow in the pump body, the free end of the gripping unit 37 has a complementary form, such as a male hexagon form.

This gripping unit 37 is advantageously in the form of a rod which the operator can manipulate by means of its proximal end, such as to rotate the rod in order to screw or unscrew the pump body in its receptacle defined by the channel delimited by the inner wall 12 of the tube.

The invention claimed is:

1. A device for securing on an opening in a ventricular wall, comprising
    a hollow main body with a generally cylindrical form with an outer surface (11),
    a ring (15) which is received at a first end of said hollow body, this ring (15) being mobile along at least part of the outer surface (11) of the hollow body,
    a tubular membrane (16) covering the outer surface (11) of the hollow body, whilst extending between said ring (15) and the end opposite the first end of the hollow body, known as the second end,
    a distal end (17) of this tubular membrane (16), placed on the side of said second end of the hollow body, being self-expandable between a first configuration in which it has a tubular form, and a second configuration in which it defines a first flange (18) extending radially, or substantially radially, starting from said hollow body, this first flange (18) being designed to abut a face of said ventricular wall,
    the other end, known as the proximal end, of this tubular membrane (16) being able to be deformed by the displacement of said ring (15) along the outer surface (11) of the hollow body, such as to form a retention flange (20), the position of which can vary relative to said first flange (18), so as to adapt to ventricular walls with different thicknesses,
    said retention flange (20) being designed to come into contact with the opposite face of said ventricular wall, such that said flanges and the assembly formed by the part of the hollow body and the portion of the tubular membrane (16) covering it, passing through said ventricular wall through said opening, lock said securing device in position in said opening.

2. The device as claimed in claim 1, wherein the proximal end of the tubular membrane (16) is configured to be deformed progressively during the displacement of the ring (15), such as to form a retention flange (20), the position of which can vary within a predetermined range of distances starting from the first flange (18).

3. The device as claimed in claim 2, wherein said ring (15) comprises on its periphery at least one coupling finger which is designed to cooperate with notches placed on the outer surface (11) of said hollow body.

4. The device as claimed in claim 2, wherein, with the outer surface (11) of said hollow body comprising a thread on at least part of its outer surface (11), the inner surface of said ring (15) comprises a thread which is configured to cooperate with said thread placed on the outer surface (11) of the hollow body, in order to permit the displacement of said ring (15).

5. The device as claimed in claim 2, wherein said ring (15) comprises a non-return finger (21) in order to prevent any loosening of the ring (15) after formation of the retention flange (20).

6. The device as claimed in claim 1, wherein said ring (15) comprises on its periphery at least one coupling finger which is designed to cooperate with notches placed on the outer surface (11) of said hollow body.

7. The device as claimed in claim 6, wherein said ring (15) comprises a non-return finger (21) in order to prevent any loosening of the ring (15) after formation of the retention flange (20).

8. The device as claimed in claim 1, wherein, with the outer surface (11) of said hollow body comprising a thread on at least part of its outer surface (11), the inner surface of said ring (15) comprises a thread which is configured to cooperate with said thread placed on the outer surface (11) of the hollow body, in order to permit the displacement of said ring (15).

9. The device as claimed in claim 8, wherein said ring (15) comprises a non-return finger (21) in order to prevent any loosening of the ring (15) after formation of the retention flange (20).

10. The device as claimed in claim 1, wherein said ring (15) comprises a non-return finger (21) in order to prevent any loosening of the ring (15) after formation of the retention flange (20).

11. The device as claimed in claim 1, wherein the outer surface (11) of the hollow body comprises a stop in order to prevent the displacement of said ring (15).

12. The device as claimed in claim 1, wherein said ring (15) and said hollow body are made of rigid materials which are inert for the human body.

13. The device as claimed in claim 1, wherein said tubular membrane (16) is made of nitinol, of a nitinol alloy, or also of expandable polyurethane.

14. The device as claimed in claim 1, configured to form a retention flange (20) with an outer diameter which is strictly larger than 3/2 D, where D is the diameter of the opening in the ventricular wall.

15. The device as claimed in claim 1, wherein with the inner wall (12) of the hollow body delimiting a channel extending between the first and second ends of the hollow body, said inner wall (12) comprises a means for a sealed connection between the body of a heart pump and said inner wall, wherein said channel is configured to partially receive the body of a heart pump.

16. The device as claimed in claim 15, wherein the means for a sealed connection comprises a thread included on the inner wall (12) configured to cooperate with a thread on an outer surface (11) of the body of the heart pump.

17. A ventricular assistance unit comprising a propulsive heart pump and a securing device as claimed in claim 1.

18. An assembly for fitting/removing a heart pump on a securing device according to claim 1, said assembly comprising a guide element with a distal end including an opening, a proximal end including an opening, and a lumen extending between the distal end opening and the proximal end opening, said heart pump having a pump body, wherein said pump body comprising a recess, said assembly comprising a gripping unit configured to slide in said lumen, wherein a free end of the gripping unit comprises a part complimentary with the recess and configured to cooperate with the recess to join the free end to the pump body in order to permit the gripping and displacement of said heart pump.

19. The assembly as claimed in claim 18, wherein the part of the free end comprises either a hollow or a projection configured to cooperate with an opposing hollow or projection to join the free end to the pump body.

20. The assembly as claimed in claim 18, wherein said pump body comprising a thread on a part of its outer surface, which is distinct from said recess, said gripping unit is an elongate body of general cylindrical shape, so as to be maneuverable in rotation in said lumen in order to screw/unscrew said pump body on a complementary thread carried by the inner wall of the hollow body.

* * * * *